(12) United States Patent
Khan

(10) Patent No.: US 9,295,254 B2
(45) Date of Patent: Mar. 29, 2016

(54) NEMATICIDES

(71) Applicant: SCIESSENT LLC, Wakefield, MA (US)

(72) Inventor: Naseem Khan, Peoria, IL (US)

(73) Assignee: SCIESSENT LLC, Wakefield, MA (US)

( * ) Notice: Subject to any disclaimer, the term of this patent is extended or adjusted under 35 U.S.C. 154(b) by 228 days.

(21) Appl. No.: 13/709,233

(22) Filed: Dec. 10, 2012

(65) Prior Publication Data

US 2013/0150439 A1 Jun. 13, 2013

Related U.S. Application Data

(60) Provisional application No. 61/568,194, filed on Dec. 8, 2011.

(51) Int. Cl.
*A01N 37/36* (2006.01)

(52) U.S. Cl.
CPC ........................................ *A01N 37/36* (2013.01)

(58) Field of Classification Search
None
See application file for complete search history.

(56) References Cited

U.S. PATENT DOCUMENTS

| | | | |
|---|---|---|---|
| 2,655,460 A | 12/1949 | Kise | |
| 3,404,987 A | 10/1968 | Kooistra et al. | |
| 4,055,655 A | 10/1977 | Maurer et al. | |
| 4,132,780 A * | 1/1979 | McConnell | 424/600 |
| 4,332,791 A | 6/1982 | Reaf et al. | |
| 4,797,274 A | 1/1989 | Miki et al. | |
| 4,906,464 A | 3/1990 | Yamamoto et al. | |
| 5,478,563 A | 12/1995 | Erami | |
| 5,804,591 A | 9/1998 | Valcke et al. | |
| 5,888,526 A | 3/1999 | Tsubai | |
| 5,968,539 A | 10/1999 | Beerse et al. | |
| 6,197,814 B1 | 3/2001 | Arata | |
| 6,294,186 B1 | 9/2001 | Beerse et al. | |
| 6,475,631 B1 | 11/2002 | Yamamoto et al. | |
| 6,482,788 B1 | 11/2002 | Arvanitidou | |
| 6,492,313 B1 | 12/2002 | Connors et al. | |
| 6,638,431 B2 | 10/2003 | Back et al. | |
| 6,689,392 B2 | 2/2004 | Lifshitz | |
| 7,049,339 B2 | 5/2006 | Thomson | |
| 7,060,302 B1 | 6/2006 | Hickok | |
| 7,147,872 B2 | 12/2006 | Ben-Yehuda et al. | |
| 7,163,709 B2 | 1/2007 | Cook et al. | |
| 7,173,049 B2 | 2/2007 | Holah et al. | |
| 8,287,893 B2 | 10/2012 | Crudden | |
| 8,802,120 B2 | 8/2014 | Crudden | |

| | | | |
|---|---|---|---|
| 2002/0025344 A1 | 2/2002 | Newman et al. | |
| 2002/0123523 A1 | 9/2002 | Arata | |
| 2003/0178374 A1 | 9/2003 | Arata | |
| 2003/0198689 A1 | 10/2003 | Arata | |
| 2004/0137076 A1 | 7/2004 | Yamauchi et al. | |
| 2004/0167220 A1 | 8/2004 | Horst et al. | |
| 2004/0176264 A1 | 9/2004 | Song et al. | |
| 2005/0079227 A1 | 4/2005 | Tate | |
| 2005/0159482 A1 | 7/2005 | Franke et al. | |
| 2005/0191365 A1 | 9/2005 | Creasey et al. | |
| 2005/0191394 A1 | 9/2005 | Cummins et al. | |
| 2005/0191395 A1 | 9/2005 | Creasey et al. | |
| 2005/0202066 A1 | 9/2005 | Arata | |
| 2006/0030506 A1 | 2/2006 | Song et al. | |
| 2006/0122082 A1 | 6/2006 | Paul | |
| 2006/0189483 A1 | 8/2006 | Hickok | |
| 2007/0087093 A1 | 4/2007 | Koefod et al. | |
| 2007/0128295 A1 | 6/2007 | Kennedy | |
| 2007/0232693 A1 | 10/2007 | Abou-Nemeh | |
| 2007/0248673 A1 | 10/2007 | Martinez et al. | |
| 2008/0292674 A1 * | 11/2008 | Crudden | 424/417 |
| 2008/0317800 A1 | 12/2008 | Amirzadoh-Asl | |
| 2009/0305888 A1 | 12/2009 | Li et al. | |

FOREIGN PATENT DOCUMENTS

| | | | |
|---|---|---|---|
| EP | 0110564 | * | 6/1984 |
| EP | 0150959 | A2 | 8/1985 |
| EP | 0189971 | A2 | 6/1986 |
| EP | 0351195 | B1 | 9/1994 |
| EP | 0648416 | A1 | 4/1995 |
| JP | 55027164 | | 2/1980 |
| JP | 55027164 | A1 | 2/1980 |
| JP | 59055177 | A1 | 3/1984 |
| JP | 61143317 | A1 | 7/1986 |
| JP | 2004131626 | A1 | 6/2004 |
| JP | 2005053794 | | 3/2005 |
| KR | 20060034258 | A | 4/2006 |
| WO | 9800012 | | 1/1998 |
| WO | 9953760 | | 10/1999 |
| WO | 0027390 | A1 | 5/2000 |
| WO | 0153444 | A1 | 7/2001 |
| WO | 0296202 | A1 | 5/2002 |
| WO | 02060248 | A2 | 8/2002 |
| WO | 03028455 | A1 | 4/2003 |
| WO | 03053170 | A1 | 7/2003 |

(Continued)

OTHER PUBLICATIONS

DuPont Kocide 3000 Product Brochure 2006.

(Continued)

*Primary Examiner* — Jennifer Berrios
(74) *Attorney, Agent, or Firm* — Edward K Welch, II; IP&L Solutions

(57) ABSTRACT

A method of treating soils to eradicate or reduce the proliferation of nematodes said method comprising the application of select metal ion-acid compositions to the soil.

20 Claims, 1 Drawing Sheet

(56) References Cited

FOREIGN PATENT DOCUMENTS

| | | | |
|---|---|---|---|
| WO | 2005023022 | A1 | 3/2005 |
| WO | 2006062845 | A2 | 6/2006 |
| WO | 2007147267 | A1 | 12/2007 |

OTHER PUBLICATIONS

DuPont Kocide 3000 "The nest copper protection is now even better!" Aug. 2006.

Gordon's Bordeaux Mixture Product Sheet / Label Jan. 2004.

* cited by examiner

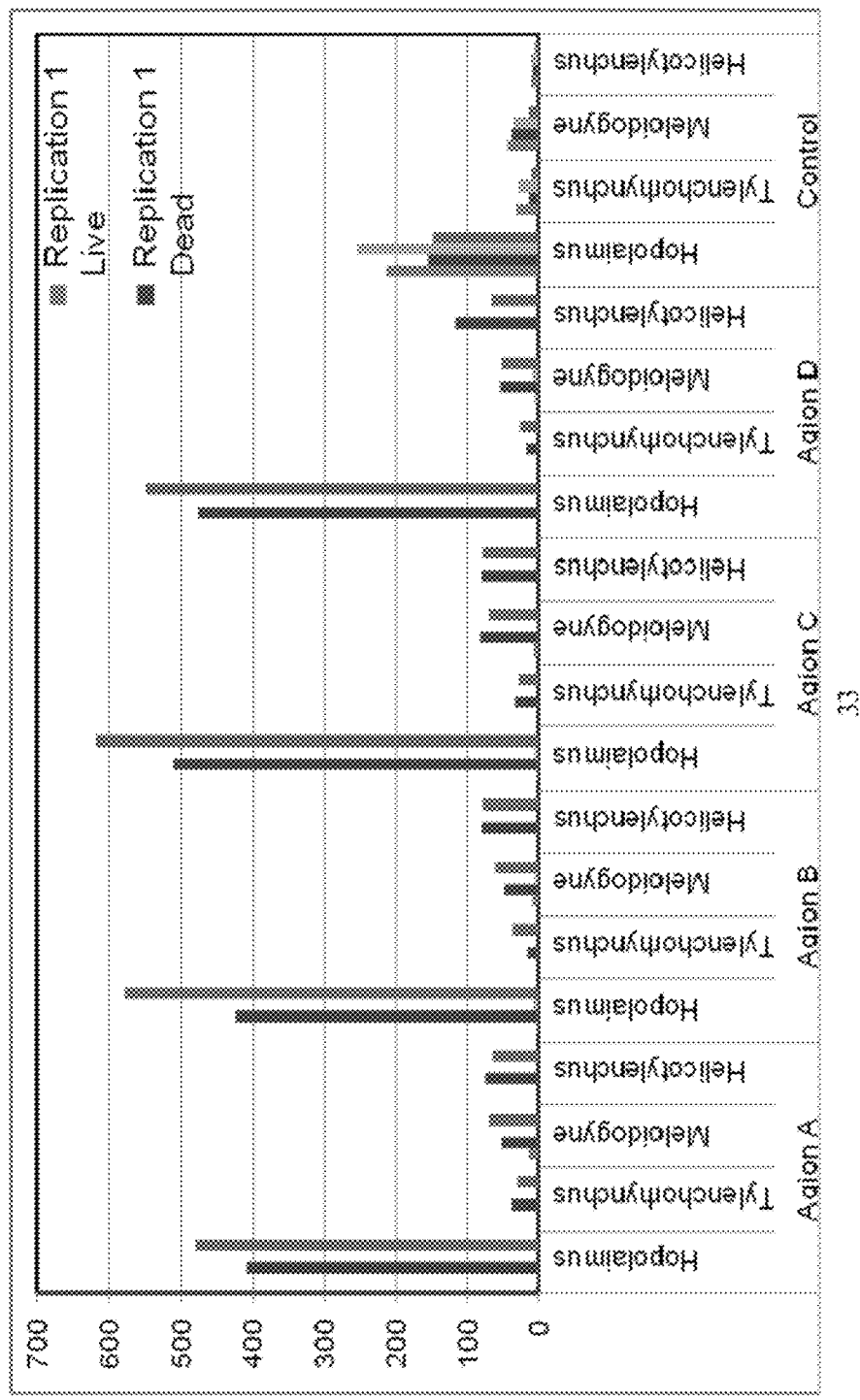

NEMATICIDES

This application claims the benefit of U.S. Provisional Patent Application No. 61/568,194 filed Dec. 8, 2011, the contents of which are hereby incorporated herein by reference in their entirety.

FIELD OF THE INVENTION

According to the present teaching there are provided new methods for eradicating and/or reducing the number and/or proliferation of nematodes, especially parasitic nematodes, from soils. Specifically, it has now been found that the application of compositions comprising one or more acids, one or more sources of nematicidal metal ions, alone or preferably in further combination with one or more surfactants, has been found to be strongly efficacious in killing nematodes when applied to infested soils, especially soils for ornamental and turf grasses.

BACKGROUND OF THE INVENTION

Nematodes are one of the world's major agricultural and horticultural pests, causing well over $80 billion in worldwide crop damage annually. These parasitic worms attack plant root systems, siphoning crucial nutrients, killing or adversely affecting the plants, diminishing the yields and the quality of the crops of crop producing plants, and making plants more susceptible or vulnerable to infection, secondary infestations, drought, and other stresses.

Traditional methods for the eradication or control of nematodes have focused on highly toxic contact and fumigant pesticides whose use have not been subject to rigid restrictions or prohibited For example, organophosphate and carbamate contact nematicides are non-specific neurotoxins and are among the most dangerous pesticides for humans, birds, fish, bees and other non-targeted organisms. Fenamiphos and carbofuran have been or are slated for banning in the United States and aldicarb is subject to sever restrictions. Methylbromide, a fumigant, since banned, is an ozone-depleting compound with broad toxicity. Other fumigants, like Metamsodium and 1,3-dichloropropene, are highly toxic and subject to rigid restrictions. Although effective, the efficacy of these fumigants is adversely affected by soils having high organic matter content, which tends to deactivate the fumigant active. The contact nematicides, on the other hand, are less effective, as the distribution of the active is less efficient than with fumigants, and to be effective, they must persist in the soil long enough to kill the nematodes. Extended persistence, however, is not desirable if there is concern with respect to residues in the crops and/or contamination of groundwater by the actives or their residues.

Thus, there remains a tremendous need for effective nematicides that eliminate or certainly lessen concern for toxicity to humans and other non-targeted organisms. Similarly, there is a tremendous, unfilled need for nematicides that can be efficaciously and effectively applied to soils and to growing plants and which are environmentally benign, or substantially so and more specific to their target organisms.

In following, there is a need for an environmentally acceptable method for the eradication and/or control of nematodes. Similarly there is a need for a method for the eradication and/or control of nematodes which does not put at risk, or at least lessens the risk to, humans and other non-target organisms.

SUMMARY OF THE INVENTION

According to the present teachings there is provided an efficacious method for the eradication and/or control of nematodes which method comprises applying a nematicidal effective amount of a composition comprising at least one acid and at least one source of at least one metal ion which has traditionally been shown to manifest antimicrobial properties, alone or in combination with at least one surfactant. This method is especially efficacious where the nematicide composition comprises at least 20 weight percent, preferably from 40 to 80 weight percent, based on the total weight of the acid and metal ion source, of the at least one acid and wherein the mole ratio of acid to metal ion is at least 0.3:1 preferably at least 2:1, most preferably at least 5:1. Most preferably, the nematicide to be applied comprises no more than about 1500 ppm, preferably no more than about 1000 ppm, most preferably no more than about 500 ppm in the case of a single metal ion and no more than about no more than about 3000 ppm, preferably no more than about 2000 ppm, most preferably no more than about 1000 ppm in the case of a multiple metal ions. Higher levels of the metal ions can be employed and are efficacious. For example, effective nematicides may have 10,000 ppm or more, even 20,000 ppm or more of the individual or combination of metal ions; however, such high concentrations lead to higher application rates and, in turn, renewed concerns for environmental harm, especially to unintended organisms, microorganisms and the plants themselves as well as residual soil and water contamination, especially with frequently repeated use. When the nematicide is applied to the soil prior to planting or plant emergence, e.g., where there is no or little concern for phytotoxicity, the pH will generally fall in the range of 1.5 to 12, inclusive, preferably 3 to 8 inclusive. However, where the nematicide is applied after planting or emergence or to turf grass and the like, the pH should be or should be adjusted to prevent or minimize any phytotoxicity. Generally, in this case the pH will be in the range of 5 to 12 inclusive, preferably 6 to 8 inclusive.

Although the method of the present teachings may employ traditional antimicrobial metal ions generally, the present findings are especially applicable to silver, zinc and copper ions as well as combinations thereof with other traditional antimicrobial metal ions, most especially to combinations of silver and zinc, silver and copper or silver, zinc and copper. Furthermore, especially where there is concern for the potential of adverse consequences to any unintended organisms, microorganisms, and the plants themselves, the acid is preferably a weak or moderate acid, most preferably a carboxylic acid or source thereof. [0008] In practicing the claimed method, the nematicide composition may be applied as a liquid which is infused into the soil or applied topically and allowed to seep into the soil. Alternatively, it may be applied as a solid which is physically worked into the soil or applied topically and allowed to slowly diffuse into the soil as a result of watering or rainfall. Liquid nematicides are generally prepared from concentrates which are let down with water or another suitable solvent or carrier. Solid nematicides may be of two types, A) solid carrier parties which are infused or treated with the liquid nematicide, whether in a dilute or concentrated form, and allowed to dry before being applied or B) a powder or dust which is formed from a cake which has been prepared from the nematicide and a cake forming carrier material which has been allowed to harden and is then crushed to form the powder, dust, or small particles which are then directly applied or mixed with additional solid particles to dilute the former and then applied. In addition, the method also contemplates the application of a dilute, light or mild acid solution to previously treated soils as the application of the acid solution will mobilize metal ions in the originally dispersed nematicide that had not or not fully dissociated and/or remobilize metal ions in those compounds which may have formed following the original application in which the metal ions formed salts and/or became bound. This subsequent acid treatment provides nematicidal effect without the further addition of metal to the soil; essentially recycling the metal already present.

In its preferred embodiment, the present method involves the application of the aforementioned composition to the soils to be treated at a level whereby the amount of the active metal ion(s), calculated as metal, applied is about 1,000 grams or less per acre, preferably, about 500 grams or less per acre, most preferably about 250 grams or less per acre. Again, higher application rates may be employed, e.g., one may apply the nematicide whereby the rate of application of the metal ion, again calculated as metal, is 10,000 grams per acre or more, even 20,000 grams per acre or more; but, once again, there is concern with respect to environmental health and safety of such high rates of use, especially when repeated use is contemplated.

DETAILED DESCRIPTION

Among the compositions suitable for use as nematicides in the practice of the presently claimed method include those antimicrobial and antifungal compositions disclosed in United States Published Patent Application numbers US 2008/0292721A1, US 2008/0292676A1 and US2008/09292723A1, US 2008/0292673A1, US2008/0292674A1 and US2008/0299222A1, all of which hereby incorporated herein by reference in their entirety. Surprisingly, it has now been found that these compositions are not only effective antimicrobial and fungicidal compositions, but are efficacious nematicides as well. However, it is to be appreciated, that suitable nematicides are not limited to those compositions but include a broader genre of compositions based on antimicrobial metal ions and acids as discussed in greater detail below.

Suitable acids that may be used in the nematicide compositions employed in the present method invention include those which are either solid or liquid in their natural state, but are readily soluble in or miscible with water or the aqueous based solvent carrier or diluent employed for application of the nematicide to the soil to be treated Suitable acids include the organic acids, especially the carboxylic acids including their salts and polyamino derivatives. Although some suitable acids fall outside of this range, it is desirable that the pKa (in water @25° C.) of the acid be greater than 0, preferably greater than 1, most preferably greater than 1.5. Exemplary organic, especially carboxylic, acids include citric acid, valeric acid, itaconic acid, acetic acid, citraconic acid, lactic acid, humic acid, malic acid, succinic acid, aldaric acid, malonic acid, proprionic acid, malonic acid, gluconic acid, maleic acid, salicylic acid, glutaric acid, tartaric acids, benzoic acid and the like; their metal salts, including potassium citrate, disodium citrate, potassium acetate, disodium acetate, especially the antimicrobial metals salts, such as copper citrate, silver citrate, zinc citrate, zinc acetate, copper acetate, silver acetate; as well as the polyamino carboxylic acids and their salts, e.g., ethylenediaminetetraacetic acid (EDTA), tripotassium ethylene diaminetetracetate ($K_3$EDTA) and disodium ethylenediamine tetraacetate ($Na_2$EDTA).

Other suitable acids include mineral acids such as nitric acid, sulfuric acid, phosphoric acid, boric acid, and the like; however, with the moderate and strong acids, especially the latter, it is preferable to buffer the acid so as to avoid handling and use problems as well as to avoid potential concerns with residual acid species if seeding and/or planting is to occur soon after application of the nematicide. In any event, if used, these acids, especially strong mineral acids like sulfuric or nitric acid should only be applied prior to seeding or planting.

The acid is generally present in the nematicide composition in an amount of at least 20 weight percent, preferably from about 40 to about 89 weight percent, based on the total weight of the acid and metal ion source. This generally coincides with a mole ratio of the acid to metal ion of at least 0.3:1, preferably at least 2:1, more preferably at least 5:1 or even 10:1. The upper limit is more of a practical limit and may exceed 20:1, event 40:1: but such levels are not necessary as it is most desirable to minimize the amount of the actives to that which is necessary to provide the desired result while minimizing costs and the potential for environmental and/or health safety concerns. These levels are typically attained by formulating nematicides whereby the acid concentration in the nematicide composition as applied or, in the case of solid nematicides, as applied to the carrier or used in making the solid nematicide is from about 0.01% to about 10%, preferably from about 0.1% to about 4% by weight of the solution. Again, higher concentrations may be used, e.g., up to 20% or more; however at such high concentrations the nematicide is preferably not being applied directly to seeds, seedlings or plants which are adversely affected by the higher acid content and/or the acid is a weak or weakly moderate acid. It is to be appreciated that where the antimicrobial metal source comprises an antimicrobial metal salts of an acid, e.g., antimicrobial metal salts of carboxylic acids, both metal ion and the acid component of those salts is considered in determining the foregoing ratios and weight percents.

The overall acidity of the compositions to be used in the present method can be important depending upon the time of application of the nematicide. For example, if the nematicide is applied prior to planting, whether seeds or seedlings, or if the seeds are acid tolerant, then the nematicide compositions may have a broad pH range, generally from about 1.5 to 12, inclusive, preferably from about 3 to 8 inclusive. However, if the nematicide is applied after planting or is applied to turf grass and the like, the pH is or is adjusted to make it less acidic to avoid phytotoxicity. Here, the pH is generally in the range of 5 to 12 inclusive, preferably 6 to 8 inclusive. In those instances where the nematicide is applied as a solid, confirmation of the pH of the solid nematicide composition is attained by dissolving the solid or mixing the solid in water to a concentration wherein the metal ion content is at its intended use application rate, i.e., 1500 ppm or less, preferably 1000 ppm or less, most preferably 500 ppm or less in the case of a single ion or 3000 ppm or less, preferably 2000 ppm or less, most preferably about 1000 ppm or less in the case or multiple antimicrobial metal ions.

The second critical component of the nematicide compositions is the metal ion or metal ion source wherein the metal ions are those conventionally known to provide efficacious antimicrobial effect: Suitable metal ions are selected from the group consisting transition metal ions and poor metal ions that have shown antimicrobial bioefficacy: such ions and metals hereinafter referred to as nematicidal ions or metals and/or antimicrobial ions or metals. Preferred metal ions are selected from the group consisting of silver, copper, zinc, mercury, tin, gold, lead, iron, bismuth, cadmium, chromium and thallium ions or combinations of any two or more of the foregoing. Most preferably, the metal ions are selected from the group consisting of silver, copper and zinc ions and combinations of any two or all three. Nematicide compositions in which at least two and preferably all three of these preferred ions are present are especially beneficial and preferred. Where multiple antimicrobial metal ions are present, each will be present in a mole fraction of 3 to 97 percent, preferably 9 to 91 percent, more preferably 20 to 80 percent. In its preferred embodiment, where multiple metal ions are present, they will be present in an amount whereby no one metal ion is more than 20 times, more preferably no more than 10 times that of any other metal ion. Especially good results have been found where each antimicrobial metal ion is present in an equal or substantially equal amount, by weight.

The metal ion is added to the acid, preferably as an aqueous solution of the acid, in the form of a source compound, salt or complex that readily releases the ions or otherwise dissociates in the acid solution or when the source and acid are dissolved in a solvent, especially water or a water-based solvent.

Exemplary salts and organometallic compounds that may suitably serve as the ion sources include the respective oxides, sulfides, carbonates, nitrates, phosphates, dihydrogen phosphates, sulfates, oxalates, quinolinolates, thiosulfates, sulfonates, phthalates, hydroxides, glycolates, and the like of the antimicrobial metals as well as the carboxylic acid salts thereof, such as the citrates, benzoates, acetates, lactates, etc. of said antimicrobial metals. Other salts such as the halide salts and substituted halide salts, including, for example, the hexafluoroantimonates, tetrafluoroborates, and perchlorates of said antimicrobial metals may be used though they are less desirable as they tend to have slow and/or poor solubility, especially in water. Specific metal salts include, but are certainly not limited to, silver nitrate, silver oxide, silver acetate, silver citrate, cupric oxide, copper hydroxide, cuprous oxide, copper oxychloride, cupric acetate, copper quinolinolate, copper citrate, zinc oxide, zinc citrate, zinc acetate, and the like.

Suitable metal ion sources also include certain inorganic complexes including, for example, those based upon an inorganic ion-exchange type carrier or dissolving glasses. It is especially preferred if the carrier or glass is soluble or at least partially soluble in the acid or diluted acid solution, especially if the solubility is controlled or a "time release" type solubility so that the metal ions are released over time: thus, providing longer term effect once applied. For example, it has been found that zeolites are readily soluble in concentrated citric acid. In the case of those carriers or glasses that are only partially soluble or slowly so, it is preferable to dissolve them in a concentrated acid solution, preferably one of from about 40% to 80% concentration, to speed up solubility.

Suitable ion-exchange type carriers include, but are not limited to, the aluminosilicates, zeolites, hydroxyapatites, and zirconium phosphates, all of which are commercially available and/or fully described in the patent literature. Each of these can be readily subjected to an ion-exchange process to bind or incorporate the desired antimicrobial metal ions. For example, antimicrobial metal ion-containing hydroxyapatite particles are described in, e.g. U.S. Pat. Nos. 5,009,898 and 5,268,174; antimicrobial metal ion-containing zirconium phosphates are described in, e.g., U.S. Pat. Nos. 4,025,608; 4,059,679; 5,296,238; 5,441,717 and 5,405,644 as well as in the Journal of Antibacterial and Antifungal Agents, Vol. 22, No. 10, pp. 595-601, 1994; and antimicrobial metal ion-containing aluminosilicates and zeolites are described in, e.g., U.S. Pat. Nos. 4,911,898; 4,911,899; 4,938,955; 4,938,958; 4,906,464; and 4,775,585, all of the aforementioned patents hereby being incorporated herein by reference in their entirety. Suitable soluble glasses include those described in, e.g., U.S. Pat. No. 5,470,585, which is also incorporated herein by reference in its entirety.

While individual metal sources may be used, it is also desirable to use combinations of metal ion sources so as to provide a mixture of metal ions. In certain instances, a single source may provide multiple metal ions. For example, preferred ion-exchange type metal ion sources include AgION AJ10D which contains both silver and zinc ions and AgION AC10D which includes both silver and copper ions.

Preferably, the metal ion sources are the readily soluble salts and compounds, as mentioned above, especially the carboxylic acid salts. Additionally, it is preferred that a combination of such compounds are employed whereby a combination of metal ions are employed, most notably combinations of silver and copper ions, silver and zinc ions or silver, zinc and copper ions. Suitable combinations include, for example, combinations of silver citrate, copper citrate and zinc citrate as well as combinations of silver nitrate, copper sulfate and zinc oxide.

The amount of the antimicrobial metal ion source to be incorporated into the acid solution or, as appropriate, to be combined with the acid is that which is sufficient to provide a concentration of about 1500 ppm or less, preferably 1000 ppm or less, most preferably 500 ppm or less in the case of a single ion or 3000 ppm or less, preferably 2000 ppm or less, most preferably about 1000 ppm or less in the case or multiple antimicrobial metal ions. Where concern exists for phytotoxicity and/or other environmental concerns for the metal release, preferred amount for the antimicrobial metal ion are from about 1 ppm to about 500 ppm, preferably from about 1 ppm to about 300 ppm, more preferably about 2 ppm to about 100 ppm, most preferably from about 5 to about 50 ppm of each antimicrobial metal in the case of a single metal ion or from about 2 ppm to about 1000 ppm, preferably from about 2 ppm to about 500 ppm, more preferably from about 5 ppm to 300 ppm, most preferably from about 5 ppm to about 150 ppm, in the case of multiple metal ions: higher levels will exist in the concentrates which are then diluted for actual in-field application. Of course, as noted above, higher levels than these can be used and are efficacious; however, it is desirable to limit the amount of metal to that necessary to provide a suitable nematicidal effect. Higher concentrations, especially those exceeding for example 10, 000 or 20,000 ppm, conflict with the desired intent of minimizing metal addition to the environment. Thus, in following with said objective, it is preferable to use the minimal, or nearly so, amount possible for the desired nematicidal effect but the claims are not so limited and the teachings are applicable to those levels that are practical for the application.

In agricultural and horticultural applications, phytotoxicity is especially of concern where the nematicide is to be applied to existing seedlings and plants. Thus, in accordance with the agricultural and horticultural applications of this invention, where the nematicide is to be applied to seedlings and plants, the level of nematicide applied should be less than would otherwise cause phytotoxicity. Most preferably, as noted above, the objective is to use as low a level as is reasonably possible yet continue to provide the nematicidal benefits desired. This concern is especially pertinent to those compositions containing copper alone or in combination with one or more of the other antimicrobial metal ions and most especially, where the bioactive acid solution or composition is to contain or be used in conjunction with another copper or copper-based material or where the same field is to be subjected to copper based fungicides during the growing cycle. In this respect, it should be noted that the aforementioned limitations on the antimicrobial metal ions refers only to those antimicrobial metal ions contributed by the one or more sources of antimicrobial metal ions associated with the bioactive acid solution or bioactive acid composition, and not to the copper or any other antimicrobial metals or metal ions that may be contributed by other compounds or materials to be used in conjunction or in combination with the nematicide compositions.

Optionally, though preferably, the nematicide compositions include one or more surfactants, especially water soluble surfactants. Especially preferred surfactants are those that affect or interact with cell walls or membranes of microorganisms, especially pathogenic microbes, or their function and/or those which aid in the movement of the actives through soil, e.g., those which may enhance solubility and/or inhibit chelating and/or binding of the metal ions. Suitable surfactants include anionic, cationic, non-ionic and amphoteric (e.g., zwitterionic) surfactants, especially those that are water soluble or show relatively good water solubility. Preferably the surfactants are anionic, non-ionic and/or amphoteric surfactants such as the sulfonates, sulfates, sulfosuccinates, sarcosinates, mono and diglycerides, amine oxides, ether carboxylates, betaines, sulfobetaines, gylcinates and the like. Though less favorable, cationic and those non-ionic surfactants having polyalkylether units, especially polyethylene oxide units, with degrees of polymerization of the alkylene ether unit of greater than about 6 may also be employed and, if so, may be used in combination with aforementioned, more effective surfactants so long as they do not materially detract from or reduce the nematicidal efficacy of the compositions.

The surfactant is typically used in conventional amounts, i.e., will be added to the nematicide compositions in an amount whereby the concentration of the surfactant in the compositions as applied is consistent their use level in traditional pesticidal compositions. Generally speaking, the surfactant will be present in an amount of from about 0.001% to about 3%, preferably from about 0.01% to about 0.5%, by weight based on the total weight of the nematicide composition. While higher loadings could be used, it is not necessary to manifest the desired nematicide efficacy. Generally, where the surfactant is basic in nature or one that hydrolyzes in water to form a basic solution, the amount should be minimized and/or the amount of acid increased so as to avoid too much neutralization of the nematicide composition.

Exemplary anionic surfactants and classes of anionic surfactants suitable for use in the practice of the present invention include: alcohol sulfates; alcohol ether sulfates; alkylaryl ether sulfates; alkylaryl sulfonates such as alkylbenzene sulfonates and alkylnaphthalene sulfonates and salts thereof; alkyl sulfonates; mono- or di-phosphate esters of polyalkoxylated alkyl alcohols or alkylphenols; mono- or di-sulfosuccinate esters of $C_{12}$ to $C_{15}$ alkanols or polyalkoxylated $C_{12}$ to $C_{15}$ alkanols; alcohol ether carboxylates; phenolic ether carboxylates; polybasic acid esters of ethoxylated polyoxyalkylene glycols consisting of oxybutylene or the residue of tetrahydrofuran; sulfoalkylamides and salts thereof such as N-methyl-N-oleoyltaurate oleoyltaurate Na salt; polyoxyalkylene alkylphenol carboxylates; polyoxyalkylene alcohol carboxylates alkyl polyglycoside/alkenyl succinic anhydride condensation products; alkyl ester sulfates; naphthalene sulfonates; naphthalene formaldehyde condensates; alkyl sulfonamides; sulfonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sultanate; ethoxylated nonylphenol phosphate ester; calcium alkylbenzene sultanate; ethoxylated tridecylalcohol phosphate ester; dialkyl sulfosuccinates, perfluoro ($C_5$-$C_{18}$)alkyl phosphonic acids; perfluoro($C_6$-$C_{18}$)alkylphosphinic acids; perfluoro($C_3$-$C_{20}$)alkyl esters of carboxylic acids; alkenyl succinic acid diglucamides; alkenyl succinic acid alkoxylates; sodium dialkyl sulfosuccinates; and alkenyl succinic acid alkylpolyglykosides.

Exemplary amphoteric and cationic surfactants include alkylpolyglycosides; betaines; sulfobetaines; glycinates; alkanol amides of $C_8$ to $C_{18}$ fatty acids and $C_8$ to $C_{18}$ fatty amine polyalkoxylates; $C_{10}$ to $C_{18}$ alkyldimethylbenzylammonium chlorides; coconut alkyldimethylaminoacetic acids; phosphate esters of $C_8$ to $C_{18}$ fatty amine polyalkoxylates; alkylpolyglycosides (APG) obtainable from a acid-catalyzed Fischer reaction of starch or glucose syrups with fatty alcohols, in particular $C_8$ to $C_{18}$ alcohols, especially the $C_8$ to $C_{18}$ and $C_{12}$ to $C_{14}$ alkylpolyglycosides having a degree of polymerization of 1.3 to 1.6, in particular 1.4 or 1.5.

Exemplary non-ionic surfactants and classes of non-ionic surfactants include: polyarylphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic dials; polyalkoxylated alkylphenols; fatty acid alkoxylates; sorbitan alkoxylates; sorbitol esters; $C_8$ to $C_{22}$ alkyl or alkenyl polyglycosides; polyalkoxy styrylaryl ethers; alkylamine oxides; block copolymer ethers; polyalkoxylated fatty glyceride; polyalkylene glycol ethers; linear aliphatic or aromatic polyesters; organo silicones; polyaryl phenols; sorbitol ester alkoxylates; and mono- and diesters of ethylene glycol and mixtures thereof; ethoxylated tristyrylphenol; ethoxylated fatty alcohol; ethoxylated lauryl alcohol; ethoxylated castor oil; and ethoxylated nonylphenol; alkoxylated alcohols, amines or acids, mixtures thereof as well as mixtures thereof with diluents and solid carriers, in particular clathrates thereof with urea. The alkoxylated alcohols, amines or acids are preferably based on alkoxy units having 2 carbon atoms, thus being a mixed ethoxylate, or 2 and 3 carbon atoms, thus being a mixed ethoxylate/propoxylated, and having at least 5 alkoxy moieties, suitably from 5 to 25 alkoxy moieties, preferably 5 to 20, in particular 5 to 15, in the alkoxy chain. The aliphatic moieties of the amine or acid alkoxylated may be straight chained or branched of 9 to 24, preferably 12 to 20, carbon atoms. The alcohol moiety of the alcohol alkoxylates is as a rule derived from a $C_9$-$C_{18}$ aliphatic alcohol, which may be non-branched or branched, especially monobranched. Preferred alcohols are typically 50% by weight straight-chained and 50% by weight branched alcohols.

As noted above, the aforementioned surfactants may be used alone or in combination. It is especially desirable to use combinations of surfactants, especially combinations which provide a synergy in the efficacy of the nematicides whether that involves an enhancement of the bioefficacy in killing or preventing the proliferation of the nematicides or the dispersion and/or movement of the nematicide actives of the presently disclosed compositions in and through the soil, or, most preferably both. All of these surfactant materials are well known and commercially available. Furthermore, those skilled in the art, without undue experimentation, will readily appreciate which surfactants and/or combinations of surfactants, in addition to the synergist surfactants, may be used for the specific end-use application, e.g., pre-planting treatment, post planting treatment, etc. Again, it is important that when additional surfactants are employed for other purposes they not interfere with or have minimal interference with the efficacy of the nematicide compositions, especially any synergy that results from the desired surfactants, i.e., those that show synergy in providing nematicide activity or a combination of nematicide and one or more antimicrobial activities when used in combination with the acid and metal ions.

If any interference exists and the other surfactant is necessary or otherwise desired for the application, then its use should be minimized to produce the least adverse impact on the nematicidal effect. Furthermore, if there is concern with such interference, especially if the surfactants are used or to be used in an amount that will neutralize the acid of the nematicide compositions so as to render them outside of the claimed range, then those surfactants may still be added but not until the time of application. In essence the nematicide compositions of the present inventions may be employed as two- or more part systems to be mixed when applied or when preparing the diluted compositions for application, which are then to be immediately applied. Most preferably, it is best to avoid the use of such surfactants or those amounts of said surfactants that will adversely affect the bioefficacy of the claimed compositions.

The nematicide compositions employed in the present teachings may be used in conjunction or in combination with one or more other conventional bioactive agrichemical actives or formulations suitable for the intended end-use, including, in particular, fungicides. It has been found that when said compositions are used concurrent with other, conventional bioactive compositions, especially fungicidal compositions, there is often a synergistic effect noted by enhanced bioefficacy, a synergy that is otherwise unexpected. For example, previously non-efficacious levels of conventional bioactive actives are rendered efficacious as a result of the presence of the bioactive acid solution or composition. Similarly, these combinations oftentimes enable one to achieve the same level of bioefficacy with less than conventional application rates or amounts of the conventional bioactive agrichemical active. Additionally, and of particular significance, the combination is also believed to reduce the incidence of and/or the speed with which bio-resistance to conventional agrichemicals, especially the synthetic organic agrichemicals, is manifested in target organisms. Thus, the commercial life expectancy of these and future conventional agrichemical actives is likely to be increased and the generation of superbugs or resistant strains of the bacterial fungi, protists and the like decreased or delayed. Such combinations of the presently disclosed nematicidal compositions and conventional agrichemicals, especially fungicides, are disclosed more fully in Published United States Patent application numbers US 2008/0292673A1, US2008/0292674A1 and US2008/0299222A1.

The bioactive agrichemical compositions according to the present invention can be used alone or, preferably and advantageously, they are used in combination with (typically as a mixture) one or more other compatible components or additives typical of agrichemical treatments and compositions including, for example, solid or liquid fillers or diluents, adjuvants, thickeners, thixotropic agents, penetrating agents, oils for spraying, stabilizers, antifreeze agents, defoaming agents, foaming agents, corrosion inhibitors, dyes, or the like, as well as other known active ingredients which have pesticidal properties (in particular fungicidal, insecticidal, acaricidal or nematicidal properties) or, in the case of in-field agricultural applications, which have plant-growth-regulating properties.

The nature and amount of the additives to be employed in the nematicide compositions depends, in part, upon the method of application and the time of application, both of which influence the form in which the composition is to take. Specifically, the nematicide composition may be in the form of and/or manufactured into e.g. emulsion concentrates, solutions, oil in water emulsions, wettable powders, soluble powders, suspension concentrates, dusts, granules, water dispersible granules, micro-capsules, gels, tablets and other formulation types by well-established procedures. The specific procedure typically includes intensive mixing and/or milling of the nematicide compositions with the other substances. The form of application such as spraying, atomizing, dispersing, dusting, pouring, infusion, and the like may be chosen based on the compositions to be applied, the time of application (e.g., pre-planting, post planting), and the given circumstances.

Although the typical definition of "filler" is a material added for the primary purpose of adding bulk, in the present application, "fillers" typically have function and utility and generally refer to organic or inorganic, natural or synthetic components with which the active components are combined to facilitate their application and to provide for a more timed or delayed or prolonged release of the active components. These fillers are generally inert and must be acceptable for the intended application, especially for agronomic uses, in particular for treating soils and plants.

The filler can be solid, for example clays, natural or synthetic silicates, silica, resins, waxes, solid fertilizers (for example ammonium salts), natural soil minerals, such as kaolins, clays, talc, lime, calcium carbonate, quartz, attapulgite, montmorillonite, bentonite or diatomaceous earths, or synthetic minerals, such as silica, alumina or silicates, in particular aluminum or magnesium silicates. The solid fillers which are suitable for granules are as follows: natural, crushed or broken rocks, such as calcites, marble, pumice, sepiolite or dolomite; synthetic granules of inorganic or organic flours; granules of organic material such as sawdust, coconut shell, corn ear or envelope, or tobacco stem; kieselguhr, tricalcium phosphate, powdered cork or adsorbent carbon black; water-soluble polymers, resins, waxes; or solid fertilizers. Such compositions can, if so desired, contain one or more compatible agents such as wetting agents, dispersing agents, emulsifiers or dyes which, when they are solid, can also act as diluents.

The fillers can also be liquids where the nematicide composition is in a concentrated form to be let down prior to application. Suitable liquid fillers include water, alcohols, in particular butanol or glycol, as well as ethers or esters thereof, in particular methyl glycol acetate; ketones, in particular acetone, cyclohexanone, methyl ethyl ketone, methyl isobutyl ketone or isophorone; petroleum fractions such as paraffinic or aromatic hydrocarbons, in particular xylenes or alkylnaphthalenes; mineral or plant oils; aliphatic chlorohydrocarbons, in particular trichloroethane or methylene chloride; aromatic chlorohydrocarbons, in particular chlorobenzenes; water-soluble or highly polar solvents such as dimethylformamide, dimethyl sulphoxide, N,N-dimethylacetamide or N-methylpyrrolidone; N-octylpyrrolidone, liquefied gases; or the like, whether they are taken separately or as a mixture. Most preferably the liquid filler or diluent is water or an aqueous based liquid.

As mentioned above, nematicide compositions employed in the claimed method will typically contain one or more additional surfactants (additional to those surfactant(s) mentioned previously that are optionally a part of the base active composition) as emulsifiers, dispersing agents, wetting agents and the like. These additional surfactants may be cationic, anionic, nonionic or amphoteric surfactants or mixtures of these surfactants. Among those surfactants which are used, for example, are polyacrylic acid salts, lignosulphonic acid salts, phenolsulphonic or naphthalenesulphonic acid salts, polycondensates of ethylene oxide with fatty alcohols or fatty acids or fatty esters or fatty amines, substituted phenols (in particular alkylphenols or arylphenols), ester-salts of sulphosuccinic acid, taurine derivatives (in particular alkyl taurates), phosphoric esters of alcohols or of polycondensates of ethylene oxide with phenols, fatty acid esters with polyols, or sulphate, sulphonate or phosphate functional derivatives of the foregoing compounds as well as those surfactants described above relative to the synergistic surfactant for the bioactive composition. Here, however, the surfactants are generally present at much higher concentrations versus that needed to show synergy with respect to the acid/metal combination. The presence of at least one additional surfactant is generally essential when the active materials and/or the inert filler are insoluble or only sparingly soluble in water and when the filler for the said composition to be applied is water. Where the nematicide is to be applied to fields in which planting has already occurred, especially where there is concern for phytotoxicity and/or contamination of the crop itself, the choice of surfactants is oftentimes paramount so as to avoid damage to and/or undesired contamination of the plant or crop. In this instance, it is desirable to select surfactants which are known to prevent the adherence of the nematicide on the foliage and which causes the nematicide to quickly run off the foliage and penetrate into the soil.

Although one would not typically want to anything that would inhibit the movement and penetration of the nematicide actives in the soil, where application coincides with anticipated rainfall; it may be desirable to slow the movement of the nematicide composition in the soil by thickening the composition. Suitable thickeners include water-soluble polymers which exhibit pseudoplastic and/or thixotropic properties in an aqueous medium such as gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, alkali metal salts of the maleic anhydride copolymers, alkali metal salts of poly (meth)acrylate, and the like. As suitable thickeners, including thixotropes, there may also be mentioned attapulgite-type clay, silica, fumed silica, carrageenan, croscarmellose sodium, furcelleran, glycerol, hydroxypropyl methylcellulose, polystyrene, vinylpyrrolidone/styrene block copolymer, hydroxypropyl cellulose, hydroxypropyl guar gum, and sodium carboxymethylcellulose. Xanthan gum is preferred.

In the case of nematicide compositions that are or may be subject to freezing during storage or use, especially aqueous and aqueous-based concentrates and solutions, it is desirable to add antifreeze additives. Specific examples of suitable antifreezes include ethylene glycol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like, in addition, ether alcohols such as diethylene glycol, triethylene glycol, tetraethylene glycol, polyoxyethylene or polyoxypropylene glycols of molecular weight up to about 4000, diethylene glycol monomethylether, diethylene glycol monoethylether, triethylene glycol monomethylether, butoxyethanol, butylene glycol monobutylether, dipentaerythritol, tripentaerythritol, tetrapentaerythritol, diglycerol, triglycerol, tetraglycerol, pentaglycerol, hexaglycerol, heptaglycerol, octaglycerol and the like. As a particular subset of suitable antifreeze materials there can be mentioned ethylene glycol, propylene glycol and glycerin.

It is possible to use dyes such as inorganic pigments, such as, for example: iron oxides, titanium oxides, Prussian blue; organic dyestuffs, such as those of the alizarin, azo or metal phthalocyanin type; or of trace elements such as iron, manganese, boron, copper, cobalt, molybdenum or zinc salts. The use of such dyes enables one to readily determine which areas have been treated with the nematicide composition. Such marking is especially important for a variety of applications and reasons. For example, in aerial, drop or broadcast application, the use of dyes allows the pilot or driver of the dispensing vehicle to quickly differentiate between those areas that have already been treated and those that have.

Although not all additives and adjuvants have been described above, those skilled in the art, particularly those skilled in the art of nematicides and other agrichemicals, will certainly appreciate what other ingredients, additives and the like would or should be used for their application. The amount by which each additive is to be incorporated into the compositions will, once again, depend upon the end-use application and the method of application and environment into which it is to be employed. Generally, though, the selection and amount is that which is conventional for such additives in such applications, e.g. nematicide applications. However, with the selection of any additives, it is important to ensure that they will not interfere with the bioactivity of the nematicide compositions or that any such interference be minimized so as to enable one to take the most advantage of the nematicidal effect. Those skilled in the art, based upon the teachings set forth herein and in the following examples, will appreciate where attention is due and, in any event, such can be addressed by simple screening applications.

As noted above, it is important to avoid the use of conventional bioactive agrichemical actives as well as any other additives and components, including those of the types mentioned above, that interfere with or adversely affect the bioefficacy of the compositions according to the present invention. Most especially, it is important to avoid the use of those agrichemical actives and other additives or compounds that are known to or will likely irreversibly or strongly sequester, bind, or complex with the antimicrobial metal ions in solution. In following, not intending to be bound by theory, it is believed that retention of the antimicrobial metal ionic charge is important for maintaining bioefficacy. For example, especially with respect to copper ions, it is best to avoid the use of ammonium salts such as ammonium sulphate, ammonium chloride, ammonium citrate, ammonium phosphate. To the extent any such materials are present or to be used, their use or, more accurately, the amount thereof, should be minimized and/or the metal ion concentration increased to offset the loss of free ions in solution compounds.

The nematicide compositions to be employed in the present method may be made by any known method for formulating agrichemical compositions generally, nematicide compositions specifically. Generally speaking, whether making a concentrate or the application ready nematicide or whether making a liquid system or a solid system, the metal acid combination, most preferably as a solution, is prepared before the addition of other conventional bioactive ingredients, if any, and/or other conventional agrichemical additives and agents.

The metal/acid solution may be prepared in a number of conventional ways. For example, each component may be mixed with or dissolved in the appropriate solvent, most notably water or a water-based solvent, and the solutions combined in the appropriate proportions. To some extent, the sequence of the addition and whether a pre-concentrate of the acid in the solvent is formed depends upon the solubility of the solids themselves. Preferably, the acid is initially dissolved in the appropriate solvent to the desired concentration. Where one is intending to form a concentrate, the amount of acid to be dissolved in the solvent should be such that the acid concentration is at least 20 percent and preferably form 40 to 80 percent. The antimicrobial metal ion source or sources are then dissolved in the concentrated acidic solution. This method may also be used in preparing a non-concentrated bioactive agrichemical composition where the rate at which the antimicrobial metal ion source or sources dissolves is increased with higher acid concentration. For example, as mentioned above, where the metal ion source is an antimicrobial metal ion containing ion-exchange type agent, especially those whose core is a zeolite, the use of concentrated acids has been found to readily dissolve the zeolite. Thereafter, the concentrated solution is merely diluted to the desired concentration after the solids are dissolved.

Where there is difficulty in dissolving the antimicrobial metal source or sources in the concentrated or dilute acid solution or the rate is undesirably slow, the antimicrobial metal ion source or sources may first be dissolved in water or another suitable aqueous-based solvent and that combined with the formed acid solution. Here, the acid solution is preferably of a higher concentration than intended in the bioactive acid solution so as to account for the dilution upon adding the dissolved antimicrobial metal ion source or sources.

Similarly, whether preparing concentrates or final, end-use formulations, it may be desirable to make individual stock solutions of each of the components of the metal/acid solution which stock solutions are then combined in the appropriate proportions. Again, the concentration of each stock solution would be tailored to account for the dilution upon their combination. Obviously, for forming concentrates, the stock solutions will typically be of higher concentration than might otherwise be necessary if using the stock solutions for preparing the final, end-use diluted formulations.

In each of the foregoing instances, the solvent/solutions may be heated and are preferably agitated to expedite the dissolving of the solids in the liquid system. Furthermore, while the dissolution of antimicrobial metal ion source or sources is perhaps the simplest and most cost effective method of the preparation of the bioactive acid solutions, these bioactive acid solutions may also be prepared by, e.g., electrolytically generating the metal ion in acid solutions as seen in Arata et. al. (U.S. Pat. No. 6,197,814; US 2003/0198689A1, US 2003/0178374A1; US2005/0245605A1 and US2006/0115440A1, all of which are incorporated herein by reference in their entirety) or by high temperature and pressure as seen in Cummins et. al. (U.S. Pat. No. 7,192,618, incorporated herein be reference).

The surfactants may be added to the metal/acid solution or the concentrate or may be added concurrent with or subsequent to the combination of the metal/acid solution with a conventional bioactive agrichemical composition, if used.

When desiring to make a liquid bioactive acid solution concentrate, one may prepare the highly concentrated solution as discussed above or make a somewhat diluted form which is then further concentrated by allowing some of the solvent to evaporate. This is particularly beneficial where the antimicrobial metal ion source or sources and/or the surfactants and/or other constituents are not soluble in and/or or are not sufficiently and/or expeditiously dissolved in the acid solution.

Depending upon the ultimate form of the nematicide composition, it may likewise be desirable to prepare a solid metal/acid composition concentrate. These solid metal/acid concentrates may also be made in a number of ways. For example, the acid, the antimicrobial metal ion source or sources and, if present, the surfactant can be dry blended. Dry blending is still possible even if the surfactant or one of the surfactants is a liquid since the amount employed is so low and will be adsorbed or absorbed by the dry materials. The dry blended materials may be employed as is or are preferably compressed to form granules. Alternatively, the solid bioactive acid composition concentrate can be formed by first preparing the bioactive acid solution concentrate mentioned above, using a volatile solvent, e.g., water or a water-base solvent, and then allowing the solvent to evaporate to leave the solid material. As necessary, the solid material is then crushed or ground to form small particles, powder or granules, of the solid bioactive acid composition. If the aforementioned materials are not able to form a stable solid, one may also add a cake forming materials, e.g., a clay or other similar material, which will help bind the active components, so that upon evaporation of the solvent, a solid cake is formed which may then be crushed, pulverized, milled, etc. to form the desired particles of the active components.

The so formed solid concentrate may be used to for a the liquid bioactive acid solution as a concentrate or as its final, end-use diluted form. In the former, the solid concentrate is dissolved in as minimal a volume of an appropriate solvent, notably water or a water based solvent, to form the concentrate. If need be or desired, especially if dissolving is hastened, a larger volume of the solvent may be employed and then partially evaporated to concentrate the materials.

The solid nematicide compositions in their final, end-use dilution may be prepared by dry blending the acid, the antimicrobial metal ion source or sources and the surfactant, if present, as well as any other optional constituents, with a solid filler material or the aforementioned solid bioactive acid composition concentrate may be let down or diluted with a solid filler material. Alternatively, and preferably, the solid nematicide is prepared by treating a filler material with the liquid nematicide composition or a liquid concentrate thereof. Here the liquid nematicide is applied to or combined with the filler material, which is preferably in particle form, and is adsorbed by and/or absorbed by the particles of the filler. For example, a mist of the nematicide solution may be sprayed or a steady or intermittent stream of the nematicide solution may be poured onto the particles as they are tumbled, stirred, etc. This embodiment has the added advantage that the amount or concentration of the liquid nematicide solution applied to the adsorbent or absorbent carrier can be higher than would be applied in the liquid diluted state so as to allow for longer term nematicide efficacy. In essence, the treated carrier serves as a reservoir of the nematicide active which are then released over time form the carrier particles. It is to be appreciated that in this embodiment, a conventional agrichemical active may also be combined into the liquid nematicide solution and applied to the carrier or the carrier may be or comprise or already contain a conventional agrichemical composition or active.

Besides the marked efficacy of the nematicide compositions with such low levels of antimicrobial metal ion, another attribute of the nematicide compositions employed in the present method is that they have no or little phytotoxicity, particularly at the higher pH range, i.e. pH 5 and above, preferably pH 6 and above. This is especially important since it allows for the application to the nematicide composition to fields that have already been planted. They also have a number of other agrichemical efficacies, such as antifungal bioefficacy, which thereby provides for multifaceted agrichemical utility and applicability. Furthermore, these compositions do not and are not likely to induce or be associated with any resistance in the target organism or in other crop pathogenic microorganisms. This contrasts sharply with the use of organic bioactive agrichemicals, especially fungicides and antibiotics, for non-nematode applications, wherein studies and actual commercial practice has shown a marked and growing tendency of resistance among the targeted organisms, even within a few years or less of their first use. The use of such agents on one species could inadvertently facilitate the development of resistant in other, non-targeted microorganisms which themselves are pathogenic or destructive to the targeted crop or other crops and could lead to catastrophic results if unchecked.

The nematicide compositions may be used to treat soils prior to planting and/or following planting, even up to the time of harvest, or in some instances, subsequent to harvest, to eradicate, control and/or prevent the proliferation of nematodes. Application at the time of or subsequent to harvest may be especially important for plants, trees and grasses that are harvested for transplant so as to avoid cross-contamination of the soil to which the plant is being transplanted with the nematodes as well as to offer a better opportunity for the transplanted plants to take, hold in their new location without conflict from the adverse effect of the nematodes. In general, the nematicide compositions may be applied to any or to soils in anticipation of the planting of a number of agricultural, including horticultural, crops including ornamental plants, shrubs and trees; flowering plants; fruiting trees, vegetable crops; feed crops; ornamental grasses and turf; etc. Exemplary food crops that are of particular concern due to their significant economic and food source impact include soy beans, tomatoes, potatoes, citrus, corn, strawberries, carrots, peppers, cotton, snap bean, lettuce, turf and greenhouse ornamentals.

The nematicide compositions may be applied in any conventional manner, spraying, dusting, spreading, soil infusion/direct injection into the soil, etc., as also noted above, or as a combined treatment of a liquid for immediate action and a solid form for a timed or delay release treatment. Typically any given formulation will be applied in the manner consistent for the crop and timing of its application. Furthermore, it is also contemplated that a conventional bioactive agent or other agrichemical additive, if any, to be used may be applied individually, concurrently or sequentially (essentially as a two-part system) with the nematicide composition. In the later instance, such sequential application will generally be within a few hours of each other, preferably within an hour or two of each other, where there is concern that the conventional bioactive agent or other agrichemical additive may interfere with the performance of the nematicide composition, e.g., adversely sequester or bind the antimicrobial metal ions. Typically though, especially for convenience and cost savings, the nematicide and any other conventional agrichemical composition, if used, will be applied as a single composition. In addition, as noted above, it is also contemplated that one may elect to apply a dilute or light or mild acid solution, e.g., an acid solution which otherwise meets the limitations for the nematicide composition less the metal ions, as a means to mobilize or remobilize metal ions of the original nematicide application which had not or not fully dissociated upon prior application and/or which formed a salt or became bound following the original application. This allows one to maximize the utilization of the metal ions while minimizing further metal input into the environment.

The rate of application of the nematicide compositions is that which provides a nematicidal effect. This will generally be such that the total amount of antimicrobial metal ions (as metal) attributed to the dissolved antimicrobial metal ion source or sources applied per acre will be about 2000 grams or less, preferably 1000 grams or less, more preferably 500 grams or less. As noted above, higher levels could be used, and are efficacious, e.g., amount on the order of 10,000 grams per acre or even 20,000 grams per acre, or more; but, these levels pose increased risk of harm to the environment and other, especially unintended organisms. Preferably, it is desirable to use as little metal as possible while maintaining nematicide efficacy, especially where there is concern for environmental contamination, most especially where the treated area is close to natural water or waterways. In these instances, it is preferred to employ rates of application on the order of 200 grams or less, preferably 100 grams or less, more preferably 50 grams or less, most preferably 20 grams or less, per acre. Of course the specific application rate and, thus, the total amount applied per acre, will vary from target organism to target organism, from one form of nematicide to another and from one application method to another. Indeed, suitable rates may be such that the total metal ion (as metal) may be on the order of 5 grams per acre, even on the order of fractions of a gram per acre, perhaps as low as 0.5 grams per acre or even 0.05 grams per acre. As noted previously, while higher loadings, higher than 2000 grams per acre, may provide even greater or faster nematicidal efficacy, the trade-off of increased environmental, health and safety concerns may not warrant or be offset by and is not typically justified by the increased, oftentimes nominal increase, in bioefficacy.

Although efficacy is most often noted by a reduced count of nematodes in the soil as compared to those soils which are untreated, one can also evaluate efficacy by an increase in yields or reduction in loss of the crop. Even a 10% improvement in yield can have a significant economic impact. In essence, even a seemingly minor reduction in the nematode count or a modest inhibition in the growth or proliferation of the nematode population can manifest an acceptable efficacy. Generally, and preferably, it is desirable to see a significant reduction, 25% or more, preferably 50% or more, in the growth or proliferation of the nematode population over two or more, preferably four or more days. More preferably, it is desirable to see an 85% or more, most preferably a 95% or more, reduction. Nevertheless, from a commercial perspective, it is to be appreciated that regardless of the numerical reduction in nematodes, the desired outcome is an increase, at least a 10% increase, preferably at least a 30% increase, most preferably a 65% increase, in yield, including healthier plants in the case or grasses, flowering plants and shrubs, and ornamentals, as compared to the untreated crop.

The following examples are presented as demonstrating the efficacy nematicide compositions and their application. These examples are merely illustrative of the invention and are not to be deemed limiting thereof. Those skilled in the art will recognize many variations that are within the spirit of the invention and scope of the claims.

For conducting the evaluation, four test compositions, A-D, were prepared, each having the formulation set forth in Table 1. These compositions were prepared by combining the ingredients and stirring the mixture until all solid components were in the solution.

TABLE 1

| COMPONENT | FORMULATION (wt %) | | | |
|---|---|---|---|---|
| | A | B | C | D |
| Citric acid | 1 | 1 | 0.5 | 0.5 |
| Silver citrate | 0.016 | 0.016 | 0.016 | 0.016 |
| Copper citrate | 0.029 | 0.029 | 0.029 | 0.029 |
| Zinc citrate | 0.025 | 0.025 | 0.025 | 0.025 |
| sodium lauryl sulfate | 0.32 | 0.16 | 0.32 | 0.16 |
| sodium lauryl sarcosinate | 0.25 | 0.125 | 0.25 | 0.125 |
| sodium hydroxide | 0.545 | 0.545 | 0.2725 | 0.2725 |
| Deionized water | 97.815 | 98.1 | 95.587 | 98.87 |

Example 1

In-vitro Immersion

In a controlled, in-vitro study, a mixture of three nematode species, *Tylenchorhynchus, Criconemella* (criconemoid) and *Helicotylenchus*, were individually subjected to a treatment with a sample of Formulations A and B and observed. The results of those observations are set forth in Table 2. In Table 2, Time 0 is the time of treatment. At 10 and 15 minutes the nematodes were transferred to clean water for formulations A and B, respectively, and observations continued. All nematodes ultimately died from the treatment,

TABLE 2

| | Time | | | | | | | |
|---|---|---|---|---|---|---|---|---|
| | 0 | 5 | 10 | 15 | 20 | 25 | 30 | 35 |
| Formulation A | | | | | | | | |
| *Tylenchorhynchus* | A | I | I | I | I | — | — | — |
| *Criconemella* | A | I | A | A | A | — | — | — |
| *Helicotylenchus* | A | I | SA | SA | I | — | — | — |
| Formulation B | | | | | | | | |
| *Tylenchorhynchus* | A | I | I | I | — | I | I | I |
| *Criconemella* | A | A | A | A | — | I | I | I |
| *Helicotylenchus* | A | I | I | I | — | I | I | I |

A—active;
SA—slightly active;
I—inactive;
"—"—no observation made

Example 2A

Soil Evaluation/Non-Diluted

Having observed the foregoing nematicidal efficacy, soil tests were conducted wherein similar soil samples of about 10 cc were taken from a golf green containing a natural population of nematodes and placed in a plastic tube having drainage. The naturally occurring nematode species were identified as *Hopolaimus, Tylenchorhynchus, Meliodogyne* and *Helicotylenchus*. Each soil sample was then subjected to treatment with Formulations A-D by pouring approximately 3 ml of each test formulation into the top of a plastic tube containing the soil sample, allowing the solution to saturate and run through the soil sample, draining away the excess formulation. After 24 hours, the soil samples were evaluated for nematode activity. No nematode activity was found: all nematodes had been killed.

Example 2B

Soil Evaluation/Diluted

A second series of experiments were conducted similar to that of Example 2A except this time dilutions of the test formulations were employed: one part formulation to four parts water. Otherwise, the testing procedure was duplicated. The results after 24 hours are presented in Table 3 and in graph form in FIG. 1. As indicated, the test formulations were highly effective against all nematode species found in the soil samples.

TABLE 3

| | | Replication 1 | | Replication 2 | |
|---|---|---|---|---|---|
| Material | Nematode | Live | Dead | Live | Dead |
| Agion A | Hoplolaimus | 4 | 410 | 0 | 480 |
| | Tylenchorhynchus | 0 | 40 | 0 | 30 |
| | Meloidogyne | 14 | 52 | 2 | 70 |
| | Helicotylenchus | 0 | 76 | 0 | 64 |
| Agion B | Hoplolaimus | 4 | 423 | 7 | 579 |
| | Tylenchorhynchus | 0 | 16 | 0 | 38 |
| | Meloidogyne | 8 | 48 | 5 | 60 |
| | Helicotylenchus | 0 | 80 | 0 | 78 |
| Agion C | Hoplolaimus | 3 | 512 | 6 | 620 |
| | Tylenchorhynchus | 0 | 34 | 0 | 28 |
| | Meloidogyne | 7 | 83 | 4 | 70 |
| | Helicotylenchus | 0 | 81 | 0 | 78 |
| Agion D | Hoplolaimus | 2 | 476 | 1 | 550 |
| | Tylenchorhynchus | 0 | 17 | 0 | 27 |
| | Meloidogyne | 5 | 54 | 9 | 52 |
| | Helicotylenchus | 0 | 116 | 0 | 67 |
| Control | Hoplolaimus | 214 | 154 | 255 | 148 |
| | Tylenchorhynchus | 32 | 14 | 28 | 10 |
| | Meloidogyne | 45 | 39 | 35 | 14 |
| | Helicotylenchus | 11 | 8 | 11 | 6 |

Example 3

Seed Treatments

Two greenhouse seed treatment evaluations were initiated on reniform nematode control on cotton (Phytogen 375 WRF) and root-knot nematode control on cucumber (Straight Eight cucumber). Both studies employed a similar set up using a randomized complete block design with two seeds planted per 4" clay pot, with the seedlings thinned to one per pot after two weeks. Six test formulations were evaluated, including the formulation A-D, with ten replications per formulation. At the time of planting, each cotton pot was inoculated with 2,500 vermiform reniform nematodes and each cucumber pot was inoculated with 2,000 root-knot nematode eggs. In both instances, the plants were fertilized weekly for the duration of the trial. The plants were harvested 40 days from planting in the case of the cotton an 34 days from planning in the case of the cucumbers.

Though favorable results were found, the overall results with the seed treatment evaluations were less conclusive than the soil treatment evaluations. In the case of the cotton seed evaluation, the plant dry weight for formulation B was significantly higher than both the inoculated and uninoculated check and formulation A had a significantly higher root dry weight than the inoculated check. However, it did not appear that any of the treatments resulted in significantly fewer eggs/g of root than the inoculated check. In the case of the cucumber seed evaluation, formulation B had fewer root-knot nematode eggs per gram of root than the inoculated check, but differences were not statistically (P=0.05) different from formulations A, C and D and none of the treatments resulted in statistically significant higher plant dry weights or root dry weights than the inoculated check. Further evaluation is contemplated and warranted relative to seed treatment applications as, again, beneficial differences were seen, but they were not markedly significant in the limited study done. This may be an indication that seed treatment is not an ideal method of application of the present formulations which, as shown above, appear best suited for application through soil drenching, granular application, and the like. Additional studies are ongoing.

Although the present invention has been described with respect to the foregoing specific embodiments and examples, it should be appreciated that other embodiments utilizing the concept of the present invention are possible without departing from the scope of the invention. Indeed, while demonstrated against turf grass nematodes, it is equally applicable to nematodes in general including cyst and lesion nematodes. The present invention is defined by the claimed elements and any and all modifications, variations, or equivalents that fall within the spirit and scope of the underlying principles.

I claim:

1. A method of treating soils to eradicate or reduce the number and/or proliferation of plant parasitic nematodes, said method comprising applying a nematicide comprising a nematicide active to the soil to be treated, said nematicide active comprising i) at least one antimicrobial metal ion or ion source which releases the antimicrobial metal ion in the presence of an acidic solution and ii) at least one organic acid, and optionally, iii) at least one surfactant which a) enhances penetration of the nematicide actives into the soil, b) enhances the bioefficacy of the nematicide actives as compared to the same nematicide actives without the surfactant, or c) both or d) a combination of such surfactants, wherein the at least one acid is present in an amount of at least 20 weight percent based on the combined weight of the acid and metal ion source and the mole ratio of acid to metal ion is at least 0.3:1, said nematicide having a pH of from about 1.5 to about 12; provided that when the nematicide is to be applied to soils in which planting has already taken place, the pH is from about 5 about 12, or the acid is sufficiently weak as not to cause phytotoxicity, wherein the nematicide does not comprise additional nematicidally active ingredients in a nematicidally effective amount.

2. The method of claim 1 wherein the antimicrobial metal ion is selected from silver ions, copper ions, zinc ions, a combination of copper and zinc ions, a combination of copper and silver ions, a combination of silver and zinc ions, a combination of copper, silver and zinc ions, and a combination of any of the foregoing and at least one other antimicrobial metal ions.

3. The meth ad of claim 1 herein the acid is a carboxylic acid.

4. The method of claim 1 wherein the acid is present in an amount of from about 40 to about 80 percent by weight based on the combined weight of the acid and metal ion source.

5. The method of claim 1 wherein the nematicide comprises up to about 20 weight percent acid and 10,000 ppm or less of the metal ions.

6. The method of claim 1 wherein the nematicide comprises from about 0.01% to about 10% of the acid, from about 1 ppm to about 1500 ppm in the case of a single antimicrobial metal ion or from 2 ppm to 3000 ppm in the case of multiple antimicrobial metal ions and, optionally, from about 0.001 to about 3 percent of the surfactant (iii).

7. The method of claim 1 wherein the metal ion is present at a concentration of from about 1 ppm to about 500 ppm in the case of a single metal ion and from about 2 to about 1000 in the case of multiple metal ions and the mole ratio of acid to metal is at least 2:1 and, optionally, from about 0.001 to about 3 percent of the surfactant (iii).

8. The method of claim 1 wherein the metal ion is present at a concentration of from about 5 ppm to about 50 ppm in the case of a single metal ion and from about 5 ppm to about 150 ppm in the case of multiple metal ions and the mole ratio of acid to metal is at least 2:1 and, optionally, from about 0.001 to about 3 percent of the surfactant (iii).

9. The method of claim 1 wherein the metal ion is at least in part derived from one or more carboxylic acid salts.

10. The method of claim 1 wherein the nematicide composition includes at least one surfactant that aids in the movement of the active components of the nematicide through the soil, at least one surfactant that enhances the performance of the active components, a combination of surfactants at least one of which aids in the movement of the active components of the nematicide through the soil and the other of which enhances the performance of the active components, or at least one surfactant that aids in the movement of the active components of the nematicide through the soil and enhances the performance of the active components.

11. The method of claim 10 wherein a combination of two or more surfactants is employed, each surfactant independently an anionic surfactant, a non-ionic surfactant or an amphoteric surfactant.

12. The method of claim 10 wherein the surfactants are selected from the group consisting of sulfonates, sulfates, sulfosuccinates, sarcosinates, mono- and di-glycerides, amine oxides, ether carboxylates, betaines, suflobetaines, and glycinates.

13. The method of claim 10 wherein the surfactants are selected from the group consisting of sulfonates, sulfates, sulfosuccinates, sarcosinates, and amine oxides.

14. The method of claim 1 wherein the nematicide is applied as an aqueous or aqueous-based solution, suspension or emulsion.

15. The method of claim 1 wherein the nematicide is applied as a solid in the form of a powder or dust comprising the nematicide actives incorporated into a suitable carrier material or in the form of solid carrier particles which have been treated with a solution of the nematicide actives or a concentrate thereof.

16. The method of claim 1 wherein the nematicide further comprises one or more antiwetting additives, dispersing agents, dyes, surfactants which cause the nematicide to run off the foliage, adjuvants, or stabilizers.

17. The method of claim 1 wherein the nematicide is applied to the soil at a rate whereby the amount of metal ions being applied is about 10,000 grams or less per acre.

18. The method of claim 1 wherein nematicide is applied to the soil at a rate whereby the amount of metal ions being applied is from about 1 gram to about 1000 grams per acre.

19. The method of claim 1 wherein nematicide is applied to the soil at a rate whereby the amount of metal ions being applied is from about 5 grams to about 500 grams per acre.

20. The method of claim 1 wherein the antimicrobial metal ion is selected from silver, copper, zinc, mercury, tin, gold, lead, iron, bismuth, cadmium, chromium and thallium ions or combinations of any two or more of the foregoing.

* * * * *